United States Patent
Cypes et al.

(10) Patent No.: US 7,326,708 B2
(45) Date of Patent: Feb. 5, 2008

(54) PHOSPHORIC ACID SALT OF A DIPEPTIDYL PEPTIDASE-IV INHIBITOR

(75) Inventors: Stephen Howard Cypes, Santa Clara, CA (US); Alex Minhua Chen, Metuchen, NJ (US); Russell R. Ferlita, Westfield, NJ (US); Karl Hansen, Atlantic Highlands, NJ (US); Ivan Lee, Piscataway, NJ (US); Vicky K. Vydra, Fair Lawn, NJ (US); Robert M. Wenslow, Jr., East Windsor, NJ (US)

(73) Assignee: Merck & Co., Inc., Rahway, NJ (US)

( * ) Notice: Subject to any disclaimer, the term of this patent is extended or adjusted under 35 U.S.C. 154(b) by 657 days.

(21) Appl. No.: 10/874,992

(22) Filed: Jun. 23, 2004

(65) Prior Publication Data

US 2005/0032804 A1    Feb. 10, 2005

Related U.S. Application Data

(60) Provisional application No. 60/482,161, filed on Jun. 24, 2003.

(51) Int. Cl.
*A61K 31/495* (2006.01)
*C07D 471/04* (2006.01)

(52) U.S. Cl. .................. 514/249; 544/350
(58) Field of Classification Search ........... 514/249; 544/350
See application file for complete search history.

(56) References Cited

U.S. PATENT DOCUMENTS

| 6,479,692 B1 * | 11/2002 | Ekwuribe et al. ........... 558/413 |
| 6,699,871 B2 | 3/2004 | Edmondson et al. |
| 2003/0100563 A1 | 5/2003 | Edmondson et al. |
| 2006/0287528 A1 * | 12/2006 | Wenslow et al. ........... 544/350 |
| 2007/0021430 A1 * | 1/2007 | Chen et al. ................ 514/249 |

FOREIGN PATENT DOCUMENTS

| WO | WO 2005/072530 A1 | 8/2005 |
| WO | WO 2006/033848 A1 | 3/2006 |

OTHER PUBLICATIONS

Edmondson, S.D., Drug Data Report, vol. 25, No. 3, pp. 245-246 (2003).
Database Prous DDR Online—Database Accession No. 2003: 3561.

* cited by examiner

*Primary Examiner*—James O. Wilson
*Assistant Examiner*—Ebenezer Sackey
(74) *Attorney, Agent, or Firm*—Philippe L. Durette; Catherine D. Fitch

(57) ABSTRACT

The dihydrogenphosphate salt of 4-oxo-4-[3-(trifluoromethyl)-5,6-dihydro [1,2,4]triazolo[4,3-a]pyrazin-7(8H)-yl]-1-(2,4,5-trifluorophenyl)butan-2-amine is a potent inhibitor of dipeptidyl peptidase-IV and is useful for the prevention and/or treatment of non-insulin dependent diabetes mellitus, also referred to as type 2 diabetes. The invention also relates to a crystalline monohydrate of the dihydrogenphosphate salt as well as a process for its preparation, pharmaceutical compositions containing this novel form and methods of use for the treatment of diabetes, obesity, and high blood pressure.

24 Claims, 5 Drawing Sheets

PHOSPHORIC ACID SALT OF A DIPEPTIDYL PEPTIDASE-IV INHIBITOR

CROSS-REFERENCE TO RELATED APPLICATIONS

The present invention is related to U.S. provisional application Ser. No. 60/482,161, filed Jun. 24, 2003, the contents of which are hereby incorporated by reference.

FIELD OF THE INVENTION

The present invention relates to a particular salt of a dipeptidyl peptidase-IV inhibitor. More particularly, the invention relates to a dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which is a potent inhibitor of dipeptidyl peptidase-IV. This novel salt and crystalline hydrates thereof are useful for the treatment and prevention of diseases and conditions for which an inhibitor of dipeptidyl peptidase-IV is indicated, in particular Type 2 diabetes, obesity, and high blood pressure. The invention further concerns pharmaceutical compositions comprising the dihydrogenphosphate salt and crystalline hydrates thereof useful to treat Type 2 diabetes, obesity, and high blood pressure as well as processes for preparing the dihydrogenphosphate salt and crystalline hydrates thereof and their pharmaceutical compositions.

BACKGROUND OF THE INVENTION

Inhibition of dipeptidyl peptidase-IV (DP-IV), an enzyme that inactivates both glucose-dependent insulinotropic peptide (GIP) and glucagon-like peptide 1 (GLP-1), represents a novel approach to the treatment and prevention of Type 2 diabetes, also known as non-insulin dependent diabetes mellitus (NIDDM). The therapeutic potential of DP-IV inhibitors for the treatment of Type 2 diabetes has been reviewed: C. F. Deacon and J. J. Holst, "Dipeptidyl peptidase IV inhibition as an approach to the treatment and prevention of Type 2 diabetes: a historical perspective," *Biochem. Biophys. Res. Commun.*, 294: 1-4 (2000); K. Augustyns, et al., "Dipeptidyl peptidase IV inhibitors as new therapeutic agents for the treatment of Type 2 diabetes," *Expert. Opin. Ther. Patents*, 13: 499-510 (2003); and D. J. Drucker, "Therapeutic potential of dipeptidyl peptidase IV inhibitors for the treatment of Type 2 diabetes," *Expert Opin. Investig. Drugs*, 12: 87-100 (2003).

WO 03/004498 (published 16 Jan. 2003), assigned to Merck & Co., describes a class of beta-amino tetrahydrotriazolo[4,3-a]pyrazines, which are potent inhibitors of DP-IV and therefore useful for the treatment of Type 2 diabetes. Specifically disclosed in WO 03/004498 is 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. Pharmaceutically acceptable salts of this compound are generically encompassed within the scope of WO 03/004498.

However, there is no specific disclosure in the above reference of the newly discovered monobasic dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine of structural formula I below.

SUMMARY OF THE INVENTION

The present invention is concerned with a novel dihydrogenphosphate salt of the dipeptidyl peptidase-IV (DP-IV) inhibitor 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and crystalline hydrates thereof, in particular a crystalline monohydrate. The dihydrogenphosphate salt and crystalline hydrates of the present invention have advantages in the preparation of pharmaceutical compositions of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, such as ease of processing, handling, and dosing. In particular, they exhibit improved physical and chemical stability, such as stability to stress, high temperatures and humidity, as well as improved physicochemical properties, such as solubility and rate of solution, rendering them particularly suitable for the manufacture of various pharmaceutical dosage forms. The invention also concerns pharmaceutical compositions containing the novel salt and hydrates as well as methods for using them as DP-IV inhibitors, in particular for the prevention or treatment of Type 2 diabetes, obesity, and high blood pressure.

DETAILED DESCRIPTION OF THE INVENTION

Figure 1:
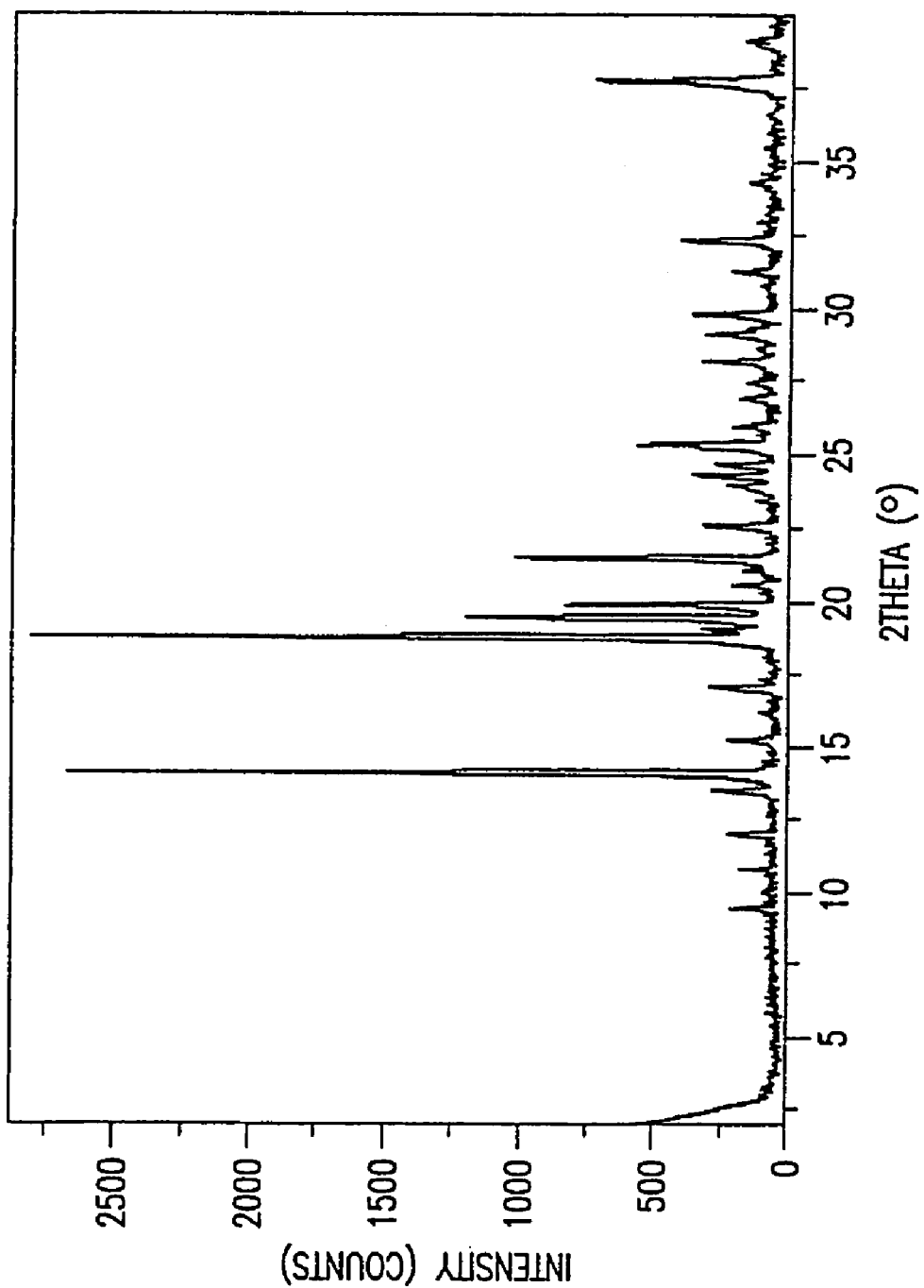
FIG. 1 is a characteristic X-ray diffraction pattern of the crystalline monohydrate of the dihydrogenphosphate salt of structural formula II.

This invention provides a new monobasic dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl) butan-2-amine of the following structural formula I:

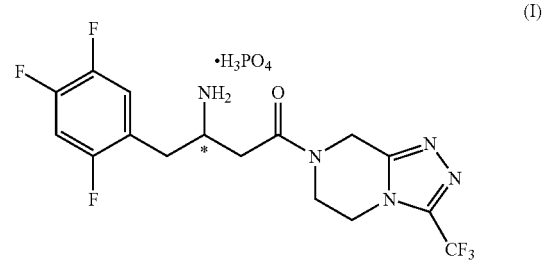

or a crystalline hydrate thereof. In particular, the instant invention provides a crystalline monohydrate of the dihydrogenphosphate salt of formula I.

The dihydrogenphosphate salt of the present invention has a center of asymmetry at the stereogenic carbon atom indicated with an * and can thus occur as a racemate, racemic mixture, and single enantiomers, with all isomeric forms being included in the present invention. The separate enantiomers, substantially free of the other, are included within the scope of the invention, as well as mixtures of the two enantiomers.

One embodiment of the present invention provides the dihydrogenphosphate salt of (2R)-4-oxo-4-[3-(trifluoromethyl)-5,6-dihydro[1,2,4]triazolo[4,3-a]pyrazin-7(8H)-yl]-1-(2,4,5-triflorophenyl) butan-2-amine of structural formula II:

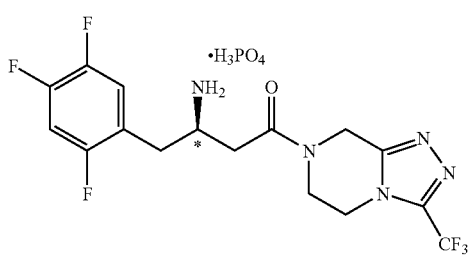

(II)

or a crystalline hydrate thereof.

A second embodiment of the present invention provides the dihydrogenphosphate salt of (2S)-4-oxo-4-[3-(trifluoromethyl)-5,6-dihydro[1,2,4]triazolo[4,3-a]pyrazin-7(8H)-yl]-1-(2,4,5-trifluorophenyl) butan-2-amine of structural formula III:

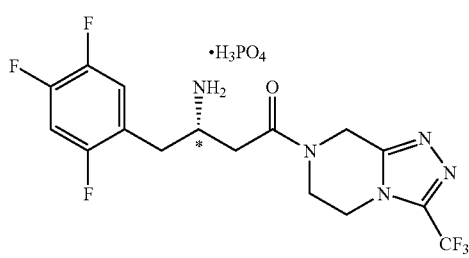

(III)

or a crystalline hydrate thereof.

More specifically, the dihydrogenphosphate salt of the present invention is comprised of one molar equivalent of mono-protonated 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine cation and one molar equivalent of dihydrogenphosphate (biphosphate) anion.

In a further embodiment of the present invention, the dihydrogenphosphate salt of structural formulae I-III is a crystalline hydrate. In one class of this embodiment, the crystalline hydrate is a crystalline monohydrate.

A further embodiment of the present invention provides the dihydrogenphosphate salt drug substance of structural formulae I-III that comprises the crystalline monohydrate present in a detectable amount. By "drug substance" is meant the active pharmaceutical ingredient ("API"). The amount of crystalline monohydrate in the drug substance can be quantified by the use of physical methods such as X-ray powder diffraction, solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. In a class of this embodiment, about 5% to about 100% by weight of the crystalline monohydrate is present in the drug substance. In a second class of this embodiment, about 10% to about 100% by weight of the crystalline monohydrate is present in the drug substance. In a third class of this embodiment, about 25% to about 100% by weight of the crystalline monohydrate is present in the drug substance. In a fourth class of this embodiment, about 50% to about 100% by weight of the crystalline monohydrate is present in the drug substance. In a fifth class of this embodiment, about 75% to about 100% by weight of the crystalline monohydrate is present in the drug substance. In a sixth class of this embodiment, substantially all of the dihydrogenphosphate salt drug substance is the crystalline monohydrate of the present invention, i.e., the dihydrogenphosphate salt drug substance is substantially phase pure monohydrate.

The crystalline dihydrogenphosphate salt of the present invention exhibits pharmaceutic advantages over the free base and the previously disclosed hydrochloride salt (WO 03/004498) in the preparation of a pharmaceutical drug product containing the pharmacologically active ingredient. In particular, the enhanced chemical and physical stability of the crystalline dihydrogenphosphate salt monohydrate constitute advantageous properties in the preparation of solid pharmaceutical dosage forms containing the pharmacologically active ingredient.

The dihydrogenphosphate salt of the present invention, which exhibits potent DP-IV inhibitory properties, is particularly useful for the prevention or treatment of Type 2 diabetes, obesity, and high blood pressure.

Another aspect of the present invention provides a method for the prevention or treatment of clinical conditions for which an inhibitor of DP-IV is indicated, which method comprises administering to a patient in need of such prevention or treatment a prophylactically or therapeutically effective amount of the dihydrogenphosphate salt of structural formula I or a hydrate thereof, in particular the crystalline monohydrate thereof. Such clinical conditions include diabetes, in particular Type 2 diabetes, hyperglycemia, insulin resistance, and obesity.

The present invention also provides the use of the dihydrogenphosphate salt of structural formula I or a hydrate thereof, in particular the crystalline monohydrate, for the manufacture of a medicament for the prevention or treatment of clinical conditions for which an inhibitor of DP-IV is indicated.

The present invention also provides pharmaceutical compositions comprising the dihydrogenphosphate salt of structural formula I or a hydrate thereof, in particular the crystalline monohydrate, in association with one or more pharmaceutically acceptable carriers or excipients. In one embodiment the pharmaceutical composition comprise a therapeutically effective amount of the active pharmaceutical ingredient in admixture with pharmaceutically acceptable excipients wherein the active pharmaceutical ingredient comprises a detectable amount of the crystalline monohydrate of the present invention. In a second embodiment the pharmaceutical composition comprise a therapeutically effective amount of the active pharmaceutical ingredient in admixture with pharmaceutically acceptable excipients wherein the active pharmaceutical ingredient comprises about 5% to about 100% by weight of the crystalline monohydrate of the present invention. In a class of this second embodiment, the active pharmaceutical ingredient in such compositions comprises about 10% to about 100% by weight of the crystalline monohydrate. In a second class of this embodiment, the active pharmaceutical ingredient in such compositions comprises about 25% to about 100% by weight of the crystalline monohydrate. In a third class of this embodiment, the active pharmaceutical ingredient in such compositions comprises about 50% to about 100% by weight of the crystalline monohydrate. In a fourth class of this embodiment, the active pharmaceutical ingredient in such compositions comprises about 75% to about 100% by weight of the crystalline monohydrate. In a fifth class of this embodiment, substantially all of the active pharmaceutical ingredient is the crystalline dihydrogenphosphate salt monohydrate of the present invention, i.e., the active pharmaceutical ingredient is substantially phase pure dihydrogenphosphate salt monohydrate.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200, and 500 milligrams of the active ingredient for the symptomatic adjustment of the dosage to the patient to be treated. A medicament typically contains from about 0.01 mg to about 500 mg of the active ingredient, preferably, from about 1 mg to about 200 mg of active ingredient. Intravenously, the most preferred doses will range from about 0.1 to about 10 mg/kg/minute during a constant rate infusion. Advantageously, the crystalline forms of the present invention may be administered in a single daily dose, or the total daily dosage may be administered in divided doses of two, three or four times daily. Furthermore, the crystalline forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the dihydrogenphosphate salt and crystalline hydrates herein described in detail can form the active pharmaceutical ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the active pharmaceutical ingredient can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The dihydrogenphosphate salt of structural formula I and the crystalline monohydrate have been found to possess a high solubility in water, rendering it especially amenable to the preparation of formulations, in particular intranasal and intravenous formulations, which require relatively concentrated aqueous solutions of active ingredient. The solubility of the crystalline dihydrogenphosphate salt monohydrate of formula I in water has been found to be about 72 mg/mL.

According to a further aspect, the present invention provides a process for the preparation of the dihydrogenphosphate salt of formula I, which process comprises reacting 4-oxo-4-[3-(trifluoromethyl)-5,6-dihydro[1,2,4]triazolo[4,3-a]pyrazin-7(8H)-yl]-1-(2,4,5-trifluoromethyl)butan-2-amine of structural formula IV below:

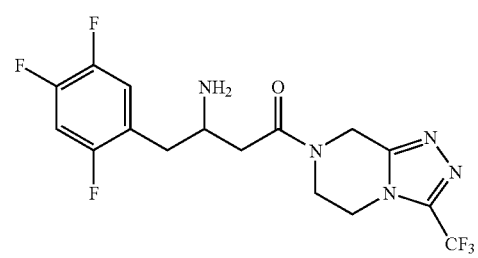

(IV)

with approximately one equivalent of phosphoric acid in a suitable $C_1$-$C_5$ alkanol, such as methanol, ethanol, isopropyl alcohol (IPA), and isoamyl alcohol (IAA) or aqueous $C_1$-$C_5$ alkanol. The reaction is carried out at a temperature range of about 25 ° C. to about 80 ° C. The phosphoric acid solution can be added to a solution of the amine, or the addition can be performed in the reverse direction. The crystalline dihydrogenphosphate salt monohydrate is obtained by crystallization from an aqueous $C_1$-$C_5$ alkanol solution of the dihydrogenphosphate salt as described below.

General Methods for Crystallizing the Monohydrate of the Dihydrogenphosphate Salt of Structural Formula I (a) In Ethanol/Water System at 25° C.:

(1) crystallization from a mixture of compound I in ethanol and water, such that the water concentration is above 31 weight percent, (2) recovering the resultant solid phase, and (3) removing the solvent therefrom.

(b) In Isoamyl Alcohol (IAA)/Water System at 25° C.:
(1) crystallization from a mixture of compound I in IAA and water, such that the water concentration is above 2.9 weight percent;
(2) recovering the resultant solid phase; and
(3) removing the solvent therefrom.

(c) In IAA/Water System at 40° C.:
(1) crystallization from a mixture of compound I in IAA and water, such that the water concentration is above 3.6 weight percent;
(2) recovering the resultant solid phase; and
(3) removing the solvent therefrom (d) In IAA/Water System at 60° C.:
(1) crystallization from a mixture of compound I in IAA and water, such that the water concentration is above 4.5 weight percent;
(2) recovering the resultant solid phase; and
(3) removing the solvent therefrom.

(e) In Isopropyl Alcohol (IPA)/Water System at 25° C.:
(1) crystallization from a mixture of compound I in IPA and water, such that the water concentration is above 7.0 weight percent;
(2) recovering the resultant solid phase; and
(3) removing the solvent therefrom (f) In IPA/Water System at 40° C.:
(1) crystallization from a mixture of compound I in EPA and water, such that the water concentration is above 8.1 weight percent;
(2) recovering the resultant solid phase; and
(3) removing the solvent therefrom.

(g) In IPA/Water System at 75° C.:
(1) crystallization from a mixture of compound I in IPA and water, such that the water concentration is above about 20 weight percent;
(2) recovering the resultant solid phase; and
(3) removing the solvent therefrom.

The starting compound of structural formula IV can be prepared by the procedures detailed in Schemes 1-3 and Example 1 below.

In a still further aspect, the present invention provides a method for the treatment and/or prevention of clinical conditions for which a DP-IV inhibitor is indicated, which method comprises administering to a patient in need of such prevention or treatment a prophylactically or therapeutically effective amount of the salt of Formula I as defined above or a crystalline hydrate thereof.

The following non-limiting Examples are intended to illustrate the present invention and should not be construed as being limitations on the scope or spirit of the instant invention.

Compounds described herein may exist as tautomers such as keto-enol tautomers. The individual tautomers as well as mixtures thereof are encompassed with compounds of structural formula I.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

EXAMPLE

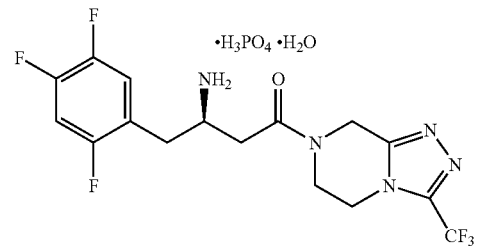

(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine dihydrogenphosphate monohydrate Preparation of 3-(trifluoromethyl)-5,6,7,8-tetrahydro[1,2,41]triazolo[4,3-a]pyrazine hydrochloride (1-4)

Scheme 1

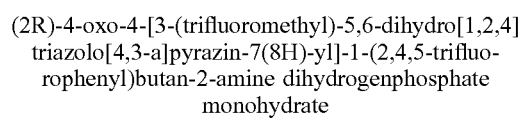

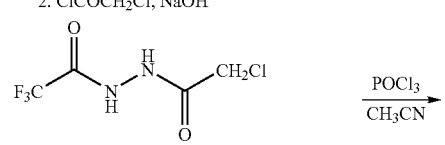

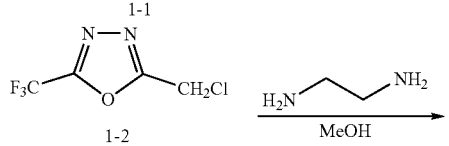

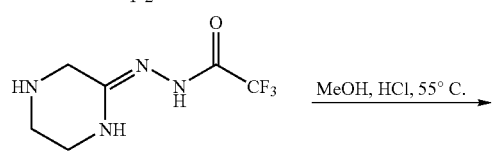

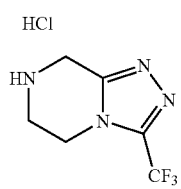

Step A: Preparation of bishydrazide (1-1)

Hydrazine (20.1 g, 35 wt% in water, 0.22 mol) was mixed with 310 mL of acetonitrile. 31.5 g of ethyl trifluoroacetate (0.22 mol) was added over 60 min. The internal temperature was increased to 25° C. from 14° C. The resulting solution was aged at 22-25° C. for 60 min. The was cooled to 7° C. 17.9 g of 50 wt % aqueous NaOH (0.22 mol) and 25.3 g of chloroacetyl chloride (0.22 mol) were added simultaneously over 130 min at a temperature below 16° C. When the reaction was complete, the mixture was vacuum distilled to remove water and ethanol at 27~30° C. and under 26 ~27 in Hg vacuum. During the distillation, 720 mL of acetonitrile was added slowly to maintain constant volume (approximately 500 mL). The slurry was filtered to remove sodium chloride. The cake was rinsed with about 100 mL of acetonitrile. Removal of the solvent afforded bis-hydrazide 1-1 (43.2 g, 96.5% yield, 94.4 area % pure by HPLC assay).

$^1$H-NMR (400 MHz, DMSO-$d_6$): δ 4.2 (s, 2H), 10.7 (s, 1H), and 11.6 (s, 1H) ppm. $^{13}$C-NMR (100 MHz, DMSO-$d_6$): δ 41.0, 116.1 (q, J=362 Hz), 155.8 (q, J=50 Hz), and 165.4 ppm.

Step B: Preparation of 5-(trifluoromethyl)-2-(chloromethyl)-1.3.4-oxadiazole (1-2)

Bishydrazide 1-1 from Step A (43.2 g, 0.21 mol) in ACN (82 mL) was cooled to 5° C. Phosphorus oxychloride (32.2 g, 0.21 mol) was added, maintaining the temperature below 10° C. The mixture was heated to 80° C. and aged at this temperature for 24 h until HPLC showed less than 2 area % of 1-1. In a separate vessel, 260 mL of IPAc and 250 mL of water were mixed and cooled to 0° C. The reaction slurry was charged to the quench keeping the internal temperature below 10° C. After the addition, the mixture was agitated vigorously for 30 min, the temperature was increased to room temperature and the aqueous layer was cut. The organic layer was then washed with 215 mL of water, 215 mL of 5 wt % aqueous sodium bicarbonate and finally 215 mL of 20 wt % aqueous brine solution. HPLC assay yield after work up was 86-92%. Volatiles were removed by distillation at 75-80 mm Hg, 55° C. to afford an oil which could be used directly in Step C without further purification. Otherwise the product can be purified by distillation to afford 1-2 in 70-80% yield.

$^1$H-NMR (400 MHz, CDCl$_3$): δ 4.8 (s, 2H) ppm. $^{13}$C-NMR (100 MHz, CDCl$_3$): δ 32.1, 115.8 (q, J=337 Hz), 156.2 (q, J=50 Hz), and 164.4 ppm.

Step C: Preparation of N-[(2Z)-piperazin-2-ylidene]trifluoroacetohydrazide (1-3)

To a solution of ethylenediamine (33.1 g, 0.55 mol) in methanol (150 mL) cooled at –20° C. was added distilled oxadiazole 1-2 from Step B (29.8 g, 0.16 mol) while keeping the internal temperature at –20° C. After the addition was complete, the resulting slurry was aged at –20° C. for 1 h. Ethanol (225 mL) was then charged and the slurry slowly warmed to –5° C. After 60 min at –5° C., the slurry was filtered and washed with ethanol (60 mL) at –5° C. Amidine 1-3 was obtained as a white solid in 72% yield (24.4 g, 99.5 area wt % pure by HPLC).

$^1$H-NMR (400 MHz, DMSO-$d_6$): δ 2.9 (t, 2H), 3.2 (t, 2H), 3.6 (s, 2H), and 8.3 (b, 1H) ppm. $^{13}$C-NMR (100 MHz, DMSO-$d_6$): δ 40.8, 42.0, 43.3, 119.3 (q, J=350 Hz), 154.2, and 156.2 (q, J=38 Hz) ppm.

Step D: Preparation of 3-(trifluoromethyl)-5,6,7,8-tetrahydro[1,2,4]triazolo[4.3-a]pyrazine hydrochloride (1-4)

A suspension of amidine 1-3 (27.3 g, 0.13 mol) in 110 mL of methanol was warmed to 55° C. 37% Hydrochloric acid (11.2 mL, 0.14 mol) was added over 15 min at this temperature. During the addition, all solids dissolved resulting in a clear solution. The reaction was aged for 30 min. The solution was cooled down to 20° C. and aged at this temperature until a seed bed formed (10 min to 1 h). 300 mL of MTBE was charged at 20° C. over 1 h. The resulting slurry was cooled to 2° C., aged for 30 min and filtered. Solids were washed with 50 mL of ethanol:MTBE (1:3) and dried under vacuum at 45° C. Yield of triazole 1-4 was 26.7 g (99.5 area wt % pure by HPLC).

$^1$H-NMR (400 MHz, DMSO-$d_6$): δ 3.6 (t, 2H), 4.4 (t, 2H), 4.6 (s, 2H), and 10.6 (b, 2H) ppm; $^{13}$C-NMR (100 MHz, DMSO-$d_6$): δ: 39.4, 39.6, 41.0, 118.6 (q, J=325 Hz), 142.9 (q, J=50 Hz), and 148.8 ppm.

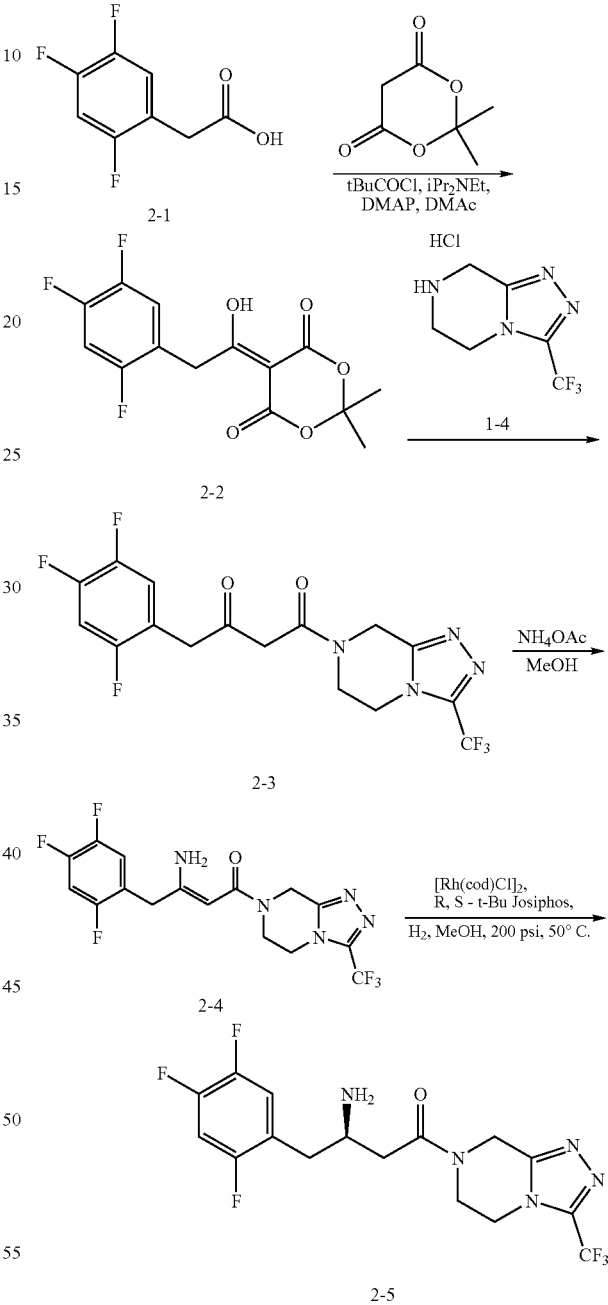

Scheme 2

Step A: Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2-3)

2,4,5-Trifluorophenylacetic acid (2-1) (150 g, 0.789 mol), Meldrum's acid (125 g, 0.868 mol), and 4-(dimethylamino) pyridine (DMAP) (7.7 g, 0063 mol) were charged into a 5 L three-neck flask. N,N-Dimethylacetamide (DMAc) (525 mL) was added in one portion at room temperature to dissolve the solids. N,N-diisopropylethylamine (282 mL, 1.62 mol) was added in one portion at room temperature while maintaining the temperature below 40° C. Pivaloyl chloride (107 mL, 0.868 mol) was added dropwise over 1 to 2 h while maintaining the temperature between 0 and 5° C. The reaction mixture was aged at 5° C. for 1 h. Triazole hydrochloride 14 (180 g, 0.789 mol) was added in one portion at 40-50° C. The reaction solution was aged at 70° C. for several h. 5% Aqueous sodium hydrogencarbonate solution (625 mL) was then added dropwise at 20-45° C. The batch was seeded and aged at 20-30° C. for 1-2 h. Then an additional 525 mL of 5% aqueous sodium hydrogencarbonate solution was added dropwise over 2-3 h. After aging several h at room temperature, the slurry was cooled to 0-5° C. and aged 1 h before filtering the solid. The wet cake was displacement-washed with 20% aqueous DMAc (300 mL), followed by an additional two batches of 20% aqueous DMAc (400 mL), and finally water (400 mL). The cake was suction-dried at room temperature. The isolated yield of final product 2-3 was 89%.

Step B: Preparation of (2Z)-4-oxo-4-[3-(trifluoromethyl)-5,6-dihydro[1,2,4]triazolo[4,3-a]pyrazin-7(8H)-yl-]-1-(2,4,5-trifluorophenyl)but-2-en-2-amine (2-4)

A 5 L round-bottom flask was charged with methanol (100 mL), the ketoamide 2-3 (200 g), and ammonium acetate (110.4 g). Methanol (180 mL) and 28% aqueous ammonium hydroxide (58.6 mL) were then added keeping the temperature below 30° C. during the addition. Additional methanol (100 mL) was added to the reaction mixture. The mixture was heated at reflux temperature and aged for 2 h. The reaction was cooled to room temperature and then to about 5° C. in an ice-bath. After 30 min, the solid was filtered and dried to afford 2-4 as a solid (180 g); m.p. 271.2° C.

Step C: Preparation of (2R)-4-oxo-4-[3-(trifluoromethyl)-5,6-dihydro[1 2,4]triazolo[4,3-a]pyrazin-7(8H)-yl]-1-(2,4,5-trifluorophenyl)butan-2-amine (2-5)

Into a 500 ml flask were charged chloro(1,5-cyclooctadiene)rhodium(I) dimer {[Rh(cod)Cl]$_2$}(292 mg, 1.18 mmol) and (R,S) t-butyl Josiphos (708 mg, 1.3 mmol) under a nitrogen atmosphere. Degassed MeOH was then added (200 mL) and the mixture was stirred at room temperature for 1 h. Into a 4 L hydrogenator was charged the enamine amide 2-4 (118 g, 0.29 mol) along with MeOH (1 L). The slurry was degassed. The catalyst solution was then transferred to the hydrogenator under nitrogen. After degassing three times, the enamine amide was hydrogenated under 200 psi hydrogen gas at 50° C. for 13 h. Assay yield was determined by HPLC to be 93% and optical purity to be 94% ee.

The optical purity was further enhanced in the following manner. The methanol solution from the hydrogenation reaction (18 g in 180 mL MeOH) was concentrated and switched to methyl t-butyl ether (MTBE) (45 mL). Into this solution was added aqueous H$_3$PO$_4$ solution (0.5 M, 95 mL). After separation of the layers, 3N NaOH (35 mL) was added to the water layer, which was then extracted with MTBE (180 mL+100 mL). The MTBE solution was concentrated and solvent switched to hot toluene (180 mL, about 75° C.). The hot toluene solution was then allowed to cool to 0° C. slowly (5-10 h). The crystals were isolated by filtration (13 g, yield 72%, 98-99% ee); m.p. 114.1-115.7° C.

$^1$H NMR (300 MHz, CD$_3$CN): δ 7.26 (m), 7.08 (m), 4.90 (s), 4.89 (s), 4.14 (m), 3.95 (m), 3.40 (m), 2.68 (m), 2.49 (m), 1.40 (bs).

Compound 2-5 exists as amide bond rotamers. Unless indicated, the major and minor rotamers are grouped together since the carbon-13 signals are not well resolved:

$^{13}$C NMR (CD$_3$CN): δ 171.8, 157.4 (ddd, J$_{CF}$=242.4, 9.2, 2.5 Hz), 152.2 (major), 151.8 (minor), 149.3 (ddd; J$_{CF}$=246.7, 14.2, 12.9 Hz), 147.4 (ddd, J$_{CF}$=241.2, 12.3, 3.7 Hz), 144.2 (q, J$_{CF}$=38.8 Hz), 124.6 (ddd, J$_{CF}$=18.5, 5.9, 4.0 Hz), 120.4 (dd, J$_{CF}$=19.1, 6.2 Hz), 119.8 (q, J$_{CF}$=268.9 Hz), 106.2(dd, J$_{CF}$=29.5, 20.9 Hz), 50.1, 44.8, 44.3 (minor), 43.2 (minor), 42.4, 41.6 (minor), 41.4, 39.6, 38.5 (minor), 36.9.

The crystalline free base can also be isolated as follows:

(a) The reaction mixture upon completion of the hydrogenation step is charged with 25 wt % of Ecosorb C-941. The mixture is stirred under nitrogen for one h and then filtered. The cake is washed with 2 L/kg of methanol. Recovery of free base is about 95% and optical purity about 95% ee.

(b) The freebase solution in methanol is concentrated to 3.5-4.0 L/kg volume (based on free base charge) and then solvent-switched into isopropanol (IPA) to final volume of 3.0 L/kg IPA.

(c) The slurry is heated to 40° C. and aged 1 h at 40° C. and then cooled to 25° C. over 2 h.

(d) Heptane (7 L/kg) is charged over 7 h and the slurry stirred for 12 h at 22-25° C. The supernatant concentration before filtering is 10-12 mg/g.

(e) The slurry is filtered and the solid washed with 30% IPA/heptane (2 L/kg).

(f) The solid is dried in a vacuum oven at 40° C.

(g) The optical purity of the free base is about 99% ee.

The following high-performance liquid chromatographic (HPLC) conditions were used to determine percent conversion to product:

Column: Waters Symmetry C18, 250 mm×4.6 mm
Eluent: Solvent A: 0.1 vol % HClO$_4$/H$_2$O
  Solvent B: acetonitrile
Gradient: 0 min 75% A: 25% B
  10 min 25% A: 75% B
  12.5 min 25% A: 75% B
  15 min 75% A: 25% B
Flow rate: 1 mL/min
Injection Vol.: 10 μL
UV detection: 210 nm
Column temp.: 40° C.
Retention times: compound 2-4: 9.1 min
  compound 2-5: 5.4 min
  tBu Josiphos: 8.7 min The following high-performance liquid chromatographic (HPLC) conditions were used to determine optical purity:

Column: Chirapak, AD-H, 250 mm×4.6 mm
Eluent: Solvent A: 0.2 vol. % diethylamine in heptane
  Solvent B: 0.1 vol % diethylamine in ethanol
Isochratic Run Time: 18 min
Flow rate: 0.7 mL/min
Injection Vol.: 7 μL
UV detection: 268 nm
Column temp.: 35° C.
Retention times: (R)-amine 2-5: 13.8 min
  (S)-amine 2-5: 11.2 min (2R)-4-oxo-4-[3-(trifluoromethyl)-5,6-dihydro[1,24]triazolo[4,3-a]pyrazin-7(8H)-yl]-1-(2,4,5-trifluorophenyl)butan-2-amine dihydrogenphosphate monohydrate A 250 mL round bottom flask equipped with an overhead stirrer, heating mantle and thermocouple, was charged with 31.5 mL of isopropanol (IPA), 13.5 mL water, 15.0 g (36.9 mmol) of (2R)-4-oxo-4-[3-(trifluoromethyl)-5,6-dihydro[1, 2,4]triazolo[4,3-a]pyrazin-7(8H)-yl]-1-(2,4,5-trifluorophenyl) butan-2-amine freebase and 4.25 g (36.9 mmol) of 85% aqueous phosphoric acid. The mixture was heated to 75° C. A thick white precipitate formed at lower temperatures but dissolved upon reaching 75° C. The solution was cooled to 68° C. and then held at that temperature for 2 h. A slurry bed of solids formed during this age time [the solution can be seeded with 0.5 to 5 wt % of small particle size (alpine milled) monohydrate]. The slurry was then cooled at a rate of 4° C./h to 21° C. and then held overnight. 105 mL of EPA was then added to the slurry. After 1 h the slurry was filtered and washed with 45 mL IPA (solids can also be washed with a water/IPA solution to avoid turnover to other crystal forms). The solids were dried on the frit with open to air. 18.6 g of solids were recovered. The solids were found to be greater than 99.8% pure by HPLC area percentage (HPLC conditions same as those given above). The particle size distribution analysis of the isolated solids showed a mean PSD of 80 microns with 95% less than 180 microns. The crystal form of the solids was shown to be monohydrate by X-ray powder diffraction and thermogravimetric analysis.

X-ray powder diffraction studies are widely used to characterize molecular structures, crystallinity, and polymorphism. The X-ray powder diffraction pattern of the crystalline dihydrogenphosphate monohydrate was generated on a Philips Analytical X'Pert PRO X-ray Diffraction System with PW3040/60 console. A PW3373/00 ceramic Cu LEF X-ray tube K-Alpha radiation was used as the source.

FIG. 1 shows the X-ray diffraction pattern for the crystalline monohydrate form of the dihydrogenphosphate salt of structural formula II. The monohydrate exhibited characteristic diffraction peaks corresponding to d-spacings of 7.42, 5.48, and 3.96 angstroms. The monohydrate was further characterized by the d-spacings of 6.30, 4.75, and 4.48 angstroms. The monohydrate was even further characterized by the d-spacings of 5.85, 5.21, and 3.52 angstroms.

In addition to the X-ray powder diffraction patterns described above, the crystalline monohydrate form of the dihydrogenphosphate salt of structural formula II was further characterized by its solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 2048 scans were collected with a recycle delay of 20 seconds. A line broadening of 40 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz, and a total of 16 scans were collected with a recycle delay of 30 seconds. A vespel endcap was utilized to minimize fluorine background. A line broadening of 100 Hz was applied to the spectrum before FT was performed. Chemical shifts are reported using poly(tetrafluoroethylene) (teflon) as an external secondary reference which was assigned a chemical shift of −122 ppm.

Figure 2:
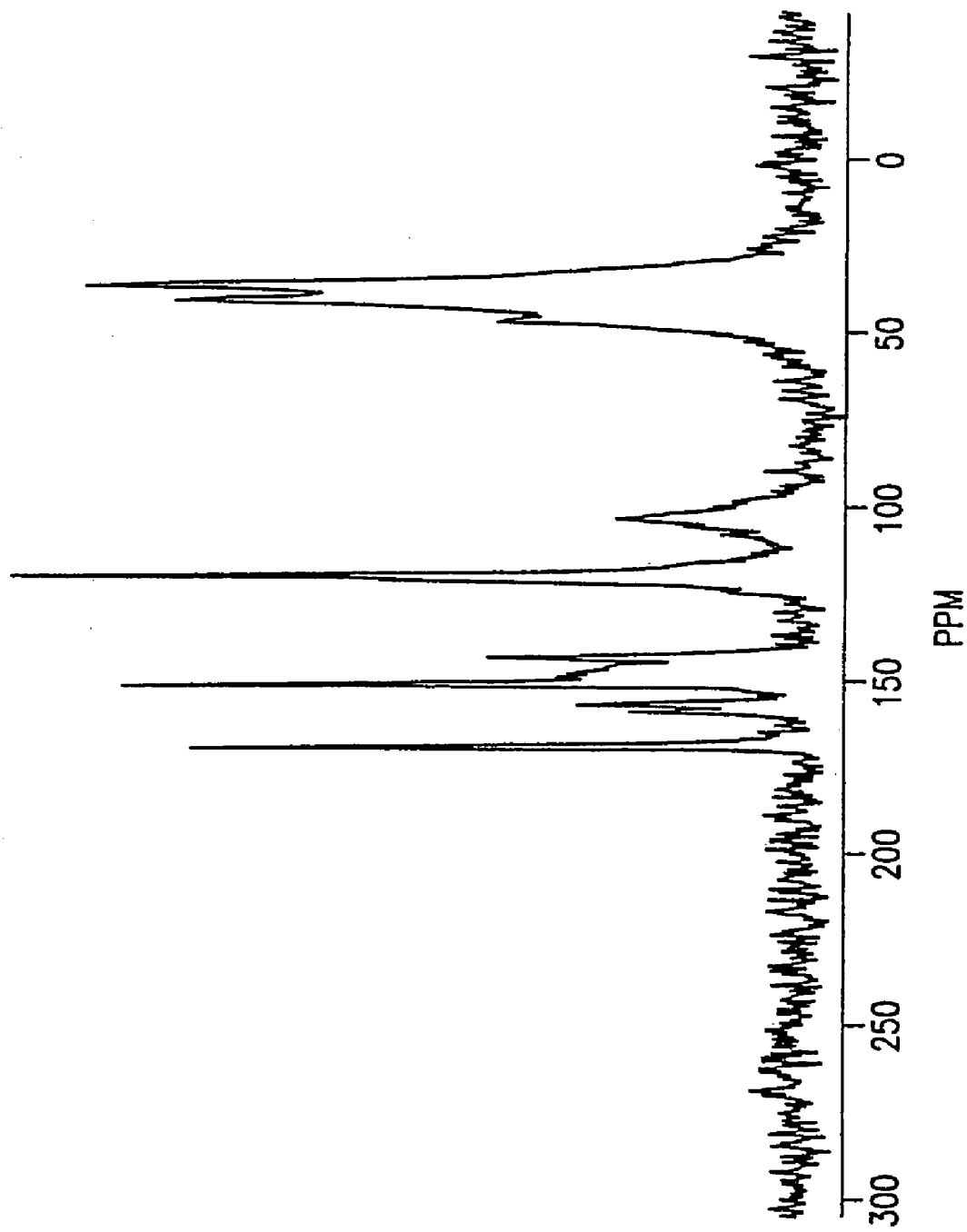
FIG. 2 is a carbon-13 cross-polarization magic-angle spinning (CPMAS) nuclear magnetic resonance (NMR) spectrum of the crystalline monohydrate of the dihydrogenphosphate salt of structural formula II.

FIG. 2 shows the solid-state carbon-13 CPMAS NMR spectrum for the crystalline monohydrate form of the dihydrogenphosphate salt of structural formula II. The monohydrate form exhibited characteristic signals with chemical shift values of 169.1, 120.8, and 46.5 p.p.m. Further characteristic of the monohydrate form were the signals with chemical shift values of 159.0, and 150.9, and 40.7 ppm.

Figure 3:
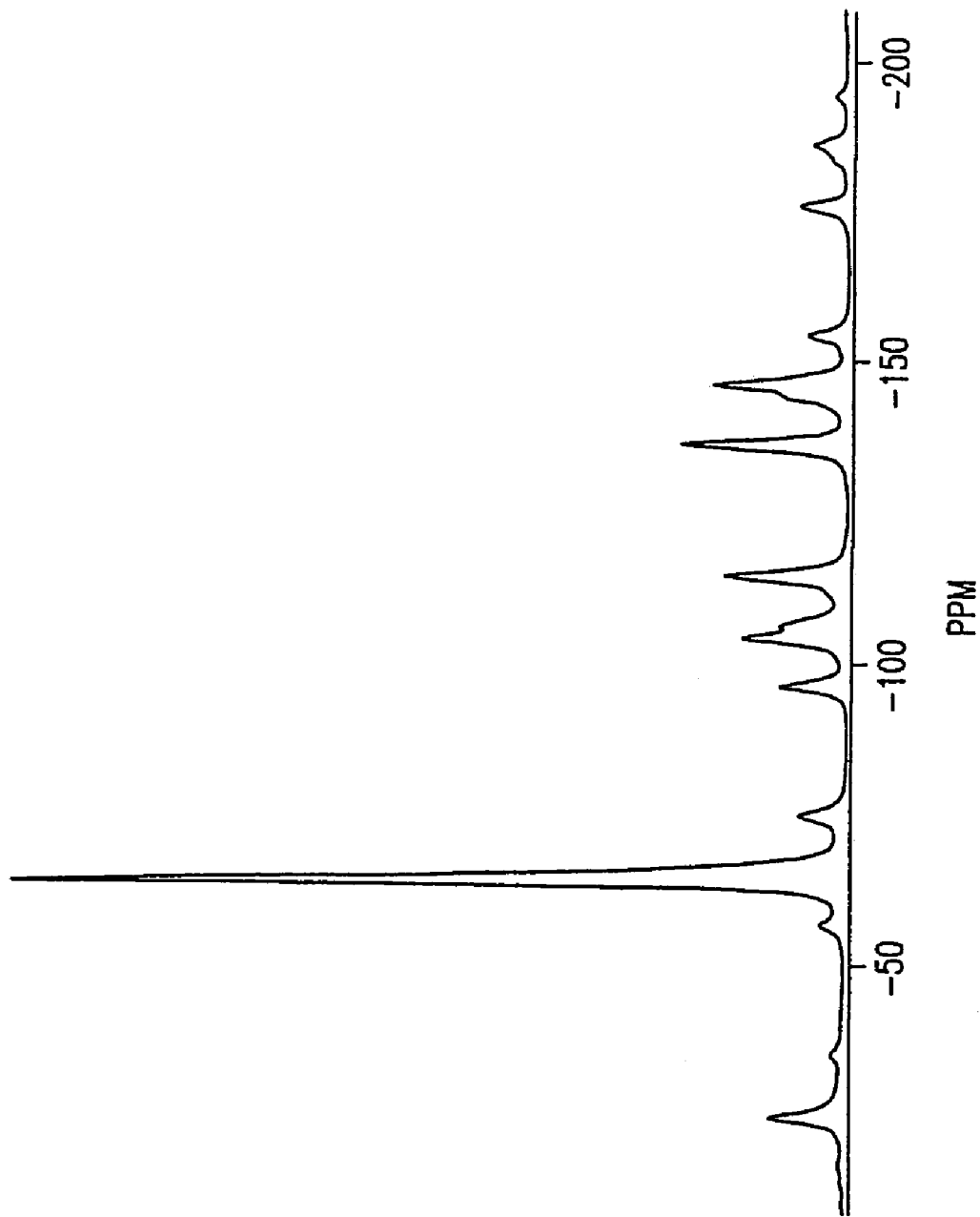
FIG. 3 is a fluorine-19 magic-angle spinning (MAS) nuclear magnetic resonance (NMR) spectrum of the crystalline monohydrate of the dihydrogenphosphate salt of structural formula II.

FIG. 3 shows the solid-state fluorine-19 MAS NM spectrum for the crystalline monohydrate form of the dihydrogenphosphate salt of structural formula II. The monohydrate form exhibited characteristic signals with chemical shift values of −64.5, −114.7, −136.3, and −146.2 p.p.m. Further characteristic of the monohydrate form were the signals with chemical shift values of −96.5, −104.4, −106.3, and −154.5 ppm.

Figure 4:
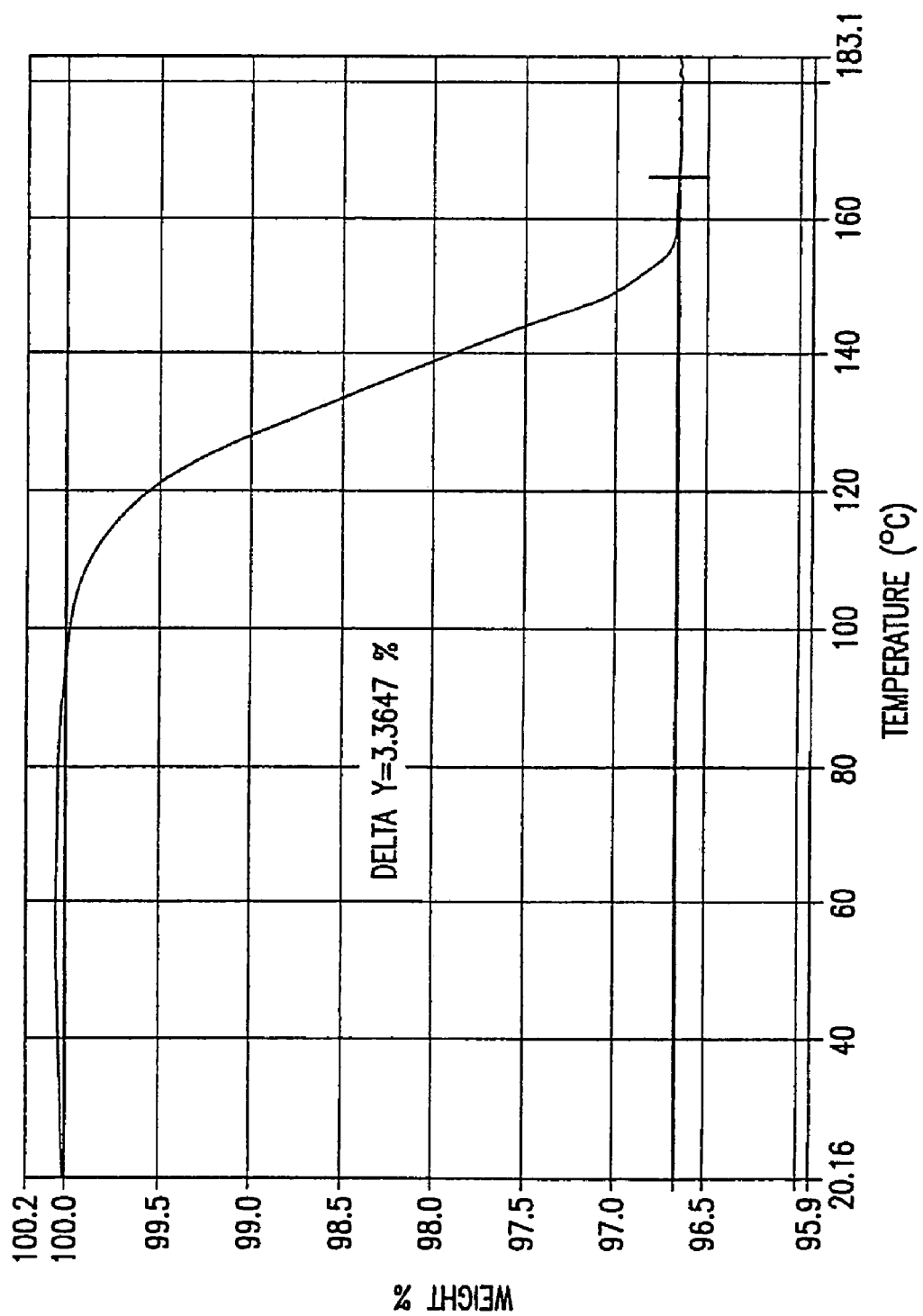
FIG. 4 is a typical thermogravimetric analysis (TGA) curve of the crystalline monohydrate dihydrogenphosphate salt of structural formula II.

FIG. 4 shows the characteristic thermogravimetric analysis (TGA) curve for the crystalline monohydrate form of the dihydrogenphosphate salt of structural formula II. A Perkin Elmer model TGA 7 or equivalent instrument was used. Experiments were performed under a flow of nitrogen and using a heating rate of 10° C./min to a maximum temperature of approximately 250° C. After automatically taring the balance, 5 to 20 mg of sample was added to the platinum pan, the furnace was raised, and the heating program started. Weight/temperature data were collected automatically by the instrument. Analysis of the results was carried out by selecting the Delta Y function within the instrument software and choosing the temperatures between which the weight loss was to be calculated. Weight losses are reported up to the onset of decomposition/evaporation. TGA indicated a weight loss of about 3.3647 % from ambient temperature to about 250° C.

Figure 5:
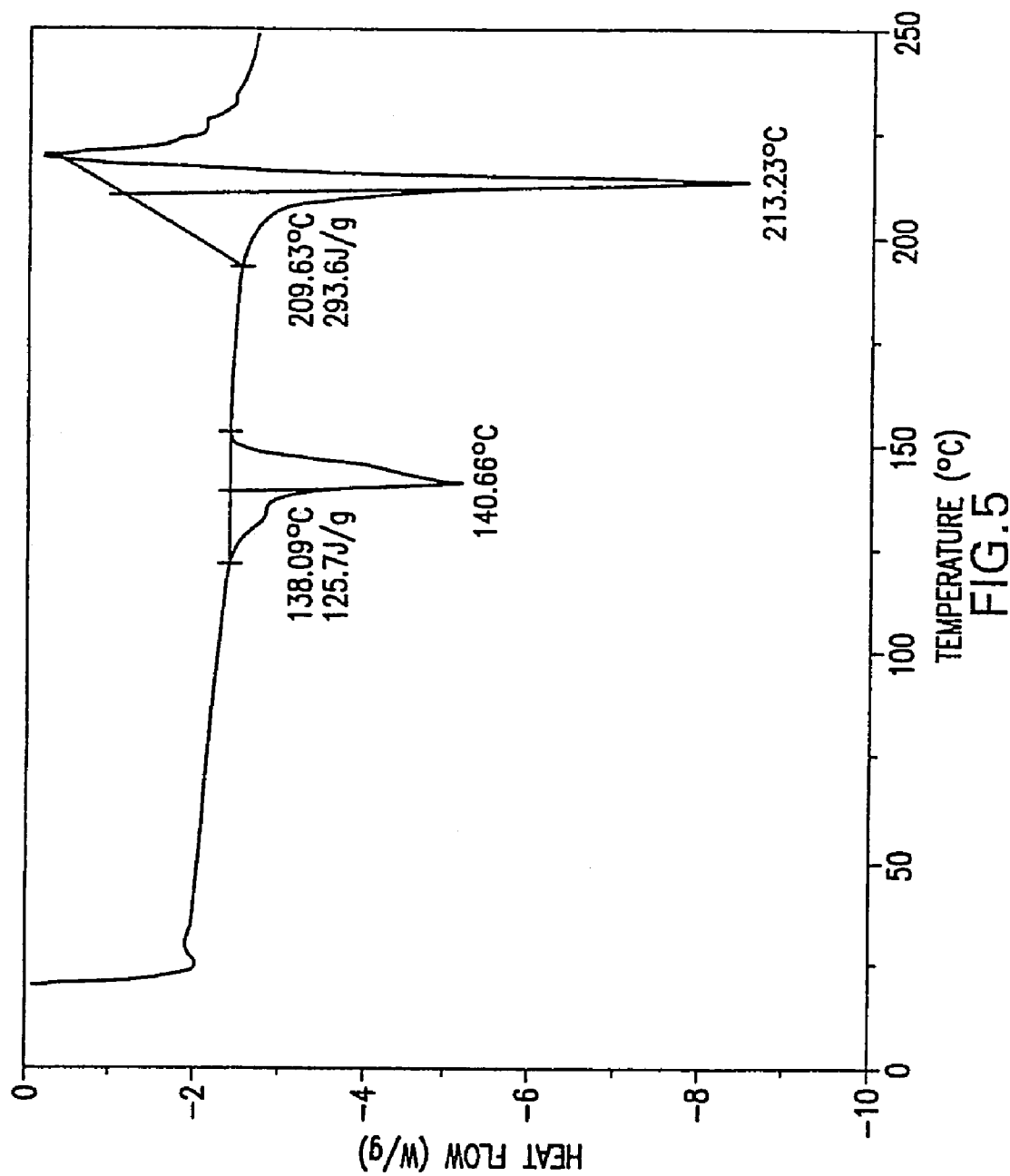
FIG. 5 is a typical differential scanning calorimetry (DSC) curve of the crystalline monohydrate of the dihydrogenphosphate salt of structural formula II.

FIG. 5 shows the characteristic DSC curve for the crystalline monohydrate form of the dihydrogenphosphate salt of structural formula II. A TA Instruments DSC 2910 or equivalent instrumentation was used. Between 2 and 6 mg sample was weighed into an open pan. This pan was then crimped and placed at the sample position in the calorimeter cell. An empty pan was placed at the reference position. The calorimeter cell was closed and a flow of nitrogen was passed through the cell. The heating program was set to heat the sample at a heating rate of 10° C./min to a temperature of approximately 250° C. The heating program was started. When the run was completed, the data were analyzed using the DSC analysis program contained in the system software. The melting endotherm was integrated between baseline temperature points that are above and below the temperature range over which the endotherm was observed. The data reported are the onset temperature, peak temperature, and enthalpy.

The crystalline dihydrogenphosphate salt monohydrate of the present invention has a phase purity of at least about 5% of the form with the above X-ray powder diffraction, fluorine-19 MAS NMR, carbon-13 CPMAS NMR, and DSC physical characteristics. In one embodiment the phase purity is at least about 10% of the form with the above solid-state physical characteristics. In a second embodiment the phase purity is at least about 25% of the form with the above solid-state physical characteristics. In a third embodiment the phase purity is at least about 50% of the form with the above solid-state physical characteristics. In a fourth embodiment the phase purity is at least about 75% of the form with the above solid-state physical characteristics. In a fifth embodiment the phase purity is at least about 90% of the form with the above solid-state physical characteristics. In a sixth embodiment the crystalline dihydrogenphosphate salt monohydrate is the substantially phase pure form with the above solid-state physical characteristics. By the term "phase purity" is meant the solid state purity of the dihydrogenphosphate salt monohydrate with regard to a particular crystalline or amorphous form of the salt as determined by the solid-state physical methods described in the present application.

The crystalline dihydrogenphosphate salt monohydrate was found to be stable under ambient condition. It was found to convert to dehydrated monohydrate if heated to above 40° C. under very dry nitrogen flow. Dehydrated monohydrate converted back to monohydrate under ambient condition.

EXAMPLES OF PHARMACEUTICAL COMPOSITIONS

1) Direct Compression Process:

The dihydrogenphosphate salt monohydrate was formulated into a tablet by a direct compression process. A 100 mg potency tablet was composed of 128.4 mg of the active ingredient, 127.8 mg microcrystalline cellulose, 127.8 mg of mannitol (or 127.8 mg of dicalcium phosphate), 8 mg of croscarmellose sodium, 8 mg of magnesium stearate and 16 mg of Opadry white (proprietary coating material made by Colorcon, West Point, Pa.). The active ingredient, microcrystalline cellulose, mannitol (or dicalcium phosphate), and croscarmellose were first blended, and the mixture was then lubricated with magnesium stearate and pressed into tablets. The tablets were then film coated with Opadry White.

2) Roller Compaction Process:

The dihydrogenphosphate salt monohydrate was formulated into a tablet by a roller compaction process. A 100 mg potency tablet was composed of 128.4 mg of the active ingredient, 45 mg microcrystalline cellulose, 111.6 mg of dicalcium phosphate, 6 mg of croscarmellose sodium, 9 mg of magnesium stearate and 12 mg of Opadry white (proprietary coating material made by Colorcon, West Point, Pa.). The active ingredient, microcrystalline cellulose, dicalcium phosphate, and croscarmellose were first blended, and the mixture was then lubricated with one third the total amount of magnesium stearate and roller compacted into ribbons. These ribbons were then milled and then resulting granules were lubricated with the remaining amount of the magnesium stearate and pressed into tablets. The tablets were then film coated with Opadry White. 3) An intravenous (i.v.) aqueous formulation is defined as the monohydrate of dihydrogenphosphate salt of formula I in 10 mM sodium acetate/ 0.8% saline solution at pH 4.5±0.2. For a formulation with a concentration of 4.0 mg/mL, 800 mg of NaCl is dissolved in 80 mL of water, then 57.5 µL of glacial acetic acid is added, followed by 512 mg of the dihydrogenphosphate salt monohydrate. The pH is adjusted to 4.5±0.2 with 0.1 N NaOH solution. The final volume is adjusted to 100 mL with water. A 2.0 mg/mL solution can be made by dilution of 50.0 mL of the 4.0 mg/mL solution to 100.0 mL with placebo. A 1.0 mg/mL solution can be made by dilution of 25.0 mL of the 4.0 mg/mL solution to 100.0 mL with placebo.

What is claimed is:

1. A dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine of structural formula I:

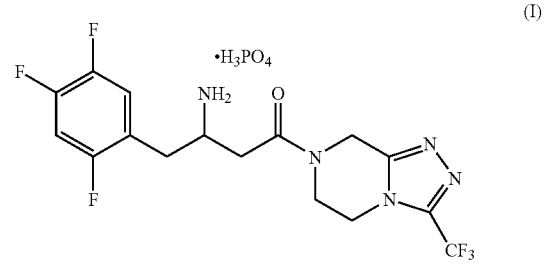

or a hydrate thereof.

2. The salt of claim 1 of structural formula II having the (R)-configuration at the chiral center marked with an *

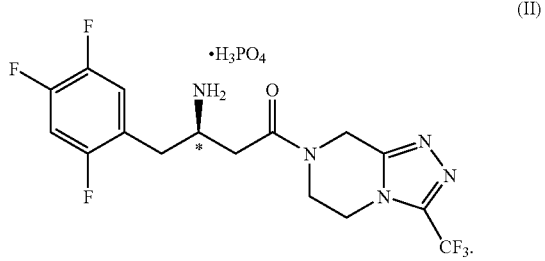

3. The salt of claim 1 of structural formula III having the (S)-configuration at the chiral center marked with an *

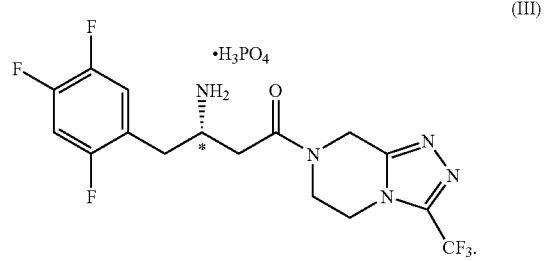

4. The salt of claim 2 characterized in being a crystalline monohydrate.

5. The salt of claim 4 characterized by characteristic absorption bands obtained from the X-ray powder diffraction pattern at spectral d-spacings of 7.42, 5.48, and 3.96 angstroms.

6. The salt of claim 5 further characterized by characteristic absorption bands obtained from the X-ray powder diffraction pattern at spectral d-spacings of 6.30, 4.75, and 4.48 angstroms.

7. The salt of claim 6 further characterized by characteristic absorption bands obtained from the X-ray powder diffraction pattern at spectral d-spacings of 5.85, 5.21, and 3.52 angstroms.

8. The salt of claim 7 further characterized by the X-ray powder diffraction pattern of FIG. 1.

9. The salt of claim 4 characterized by a solid-state carbon-13 CPMAS nuclear magnetic resonance spectrum showing signals at 169.1, 120.8, and 46.5 ppm.

10. The salt of claim 9 further characterized by a solid-state carbon-13 CPMAS nuclear magnetic resonance spectrum showing signals at 159.0, 150.9, and 40.7 ppm.

11. The salt of claim 10 further characterized by the solid-state carbon-13 CPMAS nuclear magnetic resonance spectrum of FIG. 2.

12. The salt of claim 4 characterized by a solid-state fluorine-19 MAS nuclear magnetic resonance spectrum showing signals at −64.5, −114.7, −136.3, and −146.2 ppm.

13. The salt of claim 12 further characterized by a solid-state fluorine-19 MAS nuclear magnetic resonance spectrum showing signals at −96.5, −104.4, −106.3, and −154.5 ppm.

14. The salt of claim 13 further characterized by the solid-state fluorine-19 MAS nuclear magnetic resonance spectrum of FIG. 3.

15. The salt of claim 4 characterized by the thermogravimetric analysis curve of FIG. 4.

16. The salt of claim 4 characterized by the differential scanning calorimetric curve of FIG. 5.

17. A pharmaceutical composition comprising a therapeutically effective amount of the salt according to claim 2 in association with one or more pharmaceutically acceptable carriers.

18. A pharmaceutical composition comprising a therapeutically effective amount of the salt according to claim 4 in association with one or more pharmaceutically acceptable carriers.

19. A method for the treatment of type 2 diabetes comprising administering to a patient in need of such treatment a therapeutically effective amount of the salt according to claim 2 or a hydrate thereof.

20. A method for the treatment of type 2 diabetes comprising administering to a patient in need of such treatment a therapeutically effective amount of the salt according to claim 4.

21. A process for preparing the salt of claim 2 comprising the step of contacting one equivalent of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in an organic solvent or aqueous organic solvent with about a one equivalent of phosphoric acid at a temperature in the range of about 25-100° C.

22. The process of claim 21 wherein said organic solvent is a $C_1$-$C_5$ linear or branched alkanol.

23. The phosphoric acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine prepared according to the process of claim 21.

24. A process for preparing the crystalline monohydrate of claim 4 comprising the steps of:

(a) crystallizing the dihydrogenphosphate salt of structural formula (II):

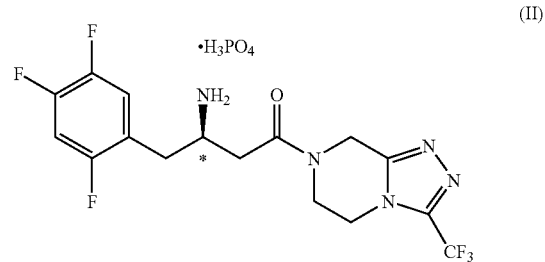

(II)

at 25° C. from a mixture of isopropanol and water, such that the water concentration is above 6.8 weight percent;

(b) recovering the resultant solid phase; and (c) removing the solvent therefrom.

* * * * *

UNITED STATES PATENT AND TRADEMARK OFFICE
CERTIFICATE OF CORRECTION

| | | |
|---|---|---|
| PATENT NO. | : 7,326,708 B2 | Page 1 of 1 |
| APPLICATION NO. | : 10/874992 | |
| DATED | : February 5, 2008 | |
| INVENTOR(S) | : Cypes et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 884 days.

Signed and Sealed this
Ninth Day of February, 2016

Michelle K. Lee
*Director of the United States Patent and Trademark Office*

UNITED STATES PATENT AND TRADEMARK OFFICE
CERTIFICATE OF CORRECTION

PATENT NO. : 7,326,708 B2
APPLICATION NO. : 10/874992
DATED : February 5, 2008
INVENTOR(S) : Stephen Howard Cypes et al.

It is certified that error appears in the above-identified patent and that said Letters Patent is hereby corrected as shown below:

In the Claims

In Column 16, Claim 5, Lines 2-3, replace "absorption bands obtained from the X-ray powder diffraction pattern at spectral" with --diffraction peaks obtained from the X-ray powder diffraction pattern corresponding to--.

In Column 16, Claim 6, Lines 2-3, replace "absorption bands obtained from the X-ray powder diffraction pattern at spectral" with --diffraction peaks obtained from the X-ray powder diffraction pattern corresponding to--.

In Column 16, Claim 7, Lines 2-3, replace "absorption bands obtained from the X-ray powder diffraction pattern at spectral" with --diffraction peaks obtained from the X-ray powder diffraction pattern corresponding to--.

Signed and Sealed this
Ninth Day of February, 2021

Drew Hirshfeld
*Performing the Functions and Duties of the
Under Secretary of Commerce for Intellectual Property and
Director of the United States Patent and Trademark Office*